United States Patent [19]
Asakawa et al.

[11] Patent Number: 5,117,109
[45] Date of Patent: May 26, 1992

[54] EXCHANGE METHOD OF MOBILE PHASE IN HIGH-PERFORMANCE LIQUID CHROMATOGRAPHY MASS SPECTROMETRY AND ITS APPARATUS

[75] Inventors: Naoki Asakawa; Hiroshi Ohe, both of Tsukuba; Yutaka Yoshida, Honjoh; Tadashi Sato, Abiko; Yukuo Nezu, Moriya; Yoshiya Oda, Tsukuba, all of Japan

[73] Assignee: Eisai Co. Ltd., Tokyo, Japan

[21] Appl. No.: 578,267

[22] Filed: Sep. 6, 1990

[30] Foreign Application Priority Data

Sep. 12, 1989 [JP] Japan ................ 1-236683

[51] Int. Cl.$^5$ .............................. B01D 59/44
[52] U.S. Cl. .......................... 250/288; 250/281; 250/282; 250/423 R; 210/198.2
[58] Field of Search ........... 750/288, 281, 283, 288 A, 750/423 R; 210/198.2

[56] References Cited

U.S. PATENT DOCUMENTS

| | | | |
|---|---|---|---|
| 3,012,139 | 12/1961 | Hanson et al. | 250/281 |
| 3,943,363 | 3/1976 | Amblard | 250/281 |
| 3,997,298 | 12/1976 | McLafferty et al. | 250/288 |
| 4,112,297 | 9/1978 | Miyagi et al. | 250/281 |
| 4,207,465 | 6/1980 | Favre et al. | 250/288 |
| 4,806,250 | 2/1989 | Takata et al. | 210/198.2 |
| 4,808,819 | 2/1989 | Hirose | 250/288 |
| 4,933,548 | 6/1990 | Boyer et al. | 250/288 |

Primary Examiner—Jack I. Berman
Assistant Examiner—Kiet T. Nguyen
Attorney, Agent, or Firm—Griffin Branigan & Butler

[57] ABSTRACT

The components present in the sample with a mobile phase A in 1st section is separated. In 2nd section there is provided with an inserting line of a dilute solution for diluting the mobile phase A and a trapping column which forces the dilute solution to pass but catches the components by connecting said line to said column. In 3rd section, the components caught by the trapping column are introduced into mass spectrometer by using a mobile phase B. It is preferable to use respectively different mobile phases for the mobile phase A and the mobile phase B. It is good to install separating columns in 1st and 3rd sections. It is also desired to add the retaining.apparatus of the components separated in 1st section.

9 Claims, 10 Drawing Sheets

→ TIME

Retention time (min)

FIG. 9

Retention time (min)

FIG. 10

Retention time (min)

EXCHANGE METHOD OF MOBILE PHASE IN HIGH-PERFORMANCE LIQUID CHROMATOGRAPHY MASS SPECTROMETRY AND ITS APPARATUS

BACKGROUND OF THE INVENTION

The present invention relates to exchange method of mobile phase in high-performance liquid chromatography mass spectrometry and apparatus constituted in such a way that the mobile phase which can introduce mobile phases and components (containing substances) suitable for the components to be separated and to be partially taken into a mass spectrometer may be freely exchanged in high-performance liquid chromatography mass spectrometry.

Figure 14:
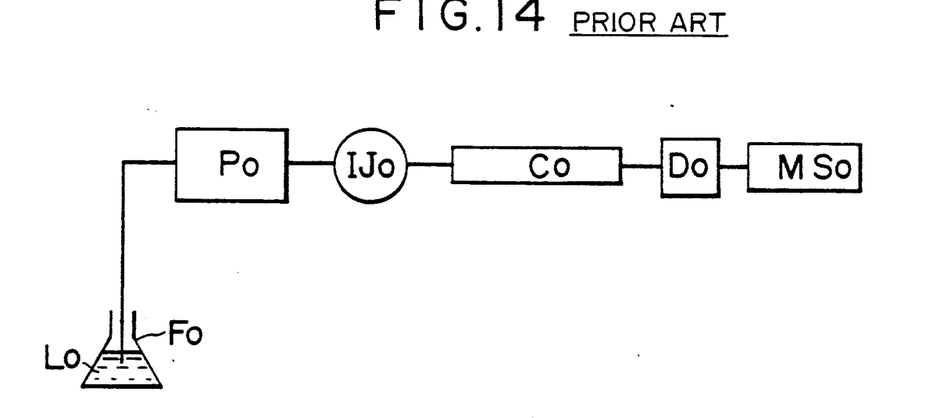
FIG. 14 indicates a conventional high-performance liquid chromatography mass spectrometric apparatus.

The conventional high-performance liquid chromatography mass spectrometry has been performed as shown in FIG. 14. That is to say, ($F_0$) is a container which has a mobile phase ($L_0$) in it, ($P_0$) is a pump, ($IJ_0$) is an injector which injects a sample to be analyzed, ($C_0$) is a separating column, ($D_0$) is a detector, ($MS_0$) is a mass spectrometer, and these are connected to each other by lines for sending liquid.

And, the apparatus is set up in such a way that the mobile phase ($L_0$) which is sent by the pump ($P_0$) as liquid is sent into the separating column ($C_0$) together with the sample injected from the injector ($IJ_0$). There components contained in the sample are separated into each component, and then introduced into the mass spectrometer ($MS_0$). The presence of the components to be introduced into the mass spectrometer ($MS_0$) can be previously detected by the detector ($D_0$).

At the introducing part of the mass spectrometer ($MS_0$), the mobile phase ($L_0$) is first removed and simultaneously the aimed components are ionized and analyzed. However, there are several methods regarding the removing means and the ionizing means, and usable mobile phases and analyzable components are restricted by some methods.

These methods include, for example, Spray method (thermo-spray method, atmospheric spray method, particle beam method), frit FAB method, and the like.

However, the conventional method has the following troubles.

A. In case of the thermospray method, the presence of an electrolyte is indispensable to ionization, and it is necessary to use a buffer for the mobile phase in the high-performance liquid chromatography mass spectrometry. With regard to buffers to be used, however, when nonvolatile buffers such as phosphate buffer and the like are used, the buffer components are deposited on the metallic nozzle of the introducing part of the mass spectrometer, and use of the mass spectrometry becomes impossible. Accordingly, for the mobile phase in the high-performance liquid chromatography mass spectrometry the volatile buffers such as ammonium acetate and the like must be used, and as a result the components to be separated are extremely restricted.

B. In case of frit FAB method, matrix to be required for ionization, for example, glycerol, ethylenediamine and the like is added to the mobile phase; however, components to be separated are extremely restricted accordingly to the kind of matrix. Also, since the buffer used in the mobile phase enters directly the mass spectrometer, said buffer is restricted to such substance which are easy to ionize the aimed components, and components to be separated are extremely limited, similar to the thermo-spray method in the high-performance liquid chromatography mass spectrometry. Therefore, aimed components which can be separated by the high-performance liquid chromatography mass spectrometry are neutral substances which can be separated without using buffers in the mobile phase or a part of ionic components (acidic or basic compounds) which can be separated in the mobile phase of volatile buffers such as ammonium acetate. Thus, the aimed components are extremely restricted. Especially, compounds used in medicines include comparatively many kinds of ionic compounds, and therefore the conventional high-performance liquid chromatography mass spectrometry can not often cope with them.

SUMMARY OF THE INVENTION

The object of the present invention is to remarkably increase the components by selecting the mobile phase respectively in the separating process of the components present in the sample and in the sending process of the components after separation to a mass spectrometer in high-performance liquid chromatography.

The above-mentioned object can be achieved by exchange method of mobile phase in high-performance liquid chromatography mass spectrometry, which is comprised of:

1st process wherein the components contained in the sample are separated by a mobile phase A;

2nd process wherein only the components of analytical object are caught by means of a trapping column after diluting the above-mentioned mobile phase A with a dilute solution; and 3rd process wherein the components of analytical object are sent to the mass spectrometer by a mobile phase B and there analyzed.

In addition, if each different mobile phase is respectively used for the mobile phase A and the mobile phase B, the optimum mobile phase can be freely selected for the component to be separated, so that the component which has not hitherto been analyzed may be analyzed.

Also, a separating column is used for separating the components contained in the sample in 1st process.

In addition, if a process is added wherein the components of analytical object caught by a trapping column are further separated in 3rd process, higher precise mass spectrometry is possible even if the aimed components are not satisfactorily separated in 1st process, and therefore the reliability of analysis can be enhanced.

Further, if a process is provided wherein the components separated in 1st process are retained, a sufficient amount of the components can be taken as a sample and the mass analysis can be performed by injecting the sample several times even if the amount of the components are present in very small quantities.

As an apparatus which actually embodies the above-mentioned object of the present invention, there is used an exchange apparatus of mobile phase in high-performance liquid chromatography mass spectrometry;

which is comprised of:

1st section wherein the components present in the sample with the mobile phase A, are separated;

2nd section comprising an inserting line of the dilute solution which dilutes the above-mentioned mobile phase A, and a trapping column which forces the above-mentioned mobile phase to pass through but catches the components by connecting said column to said line; and 3rd section wherein the components caught by the trapping column are introduced into the mass spectrometer by 3rd mobile phase.

As mentioned above, the optimum mobile phase for the component to be separated can be freely selected on-line by the present exchange method of mobile phase in high-performance liquid chromatography mass spectrometry and by the apparatus of this invention. Therefore, the components which have not been hitherto analyzed may be analyzed. Moreover, individual valves, pumps, and the like can be optionally controlled, and the operation performance is remarkably excellent.

BRIEF DESCRIPTION OF THE DRAWINGS

The above and other objects of the invention will be seen by reference to the description taken in connection with the accompanying drawings, in which.

DETAILED DESCRIPTION OF THE INVENTION

Examples of the present invention shall be illustrated below.

Figure 1:
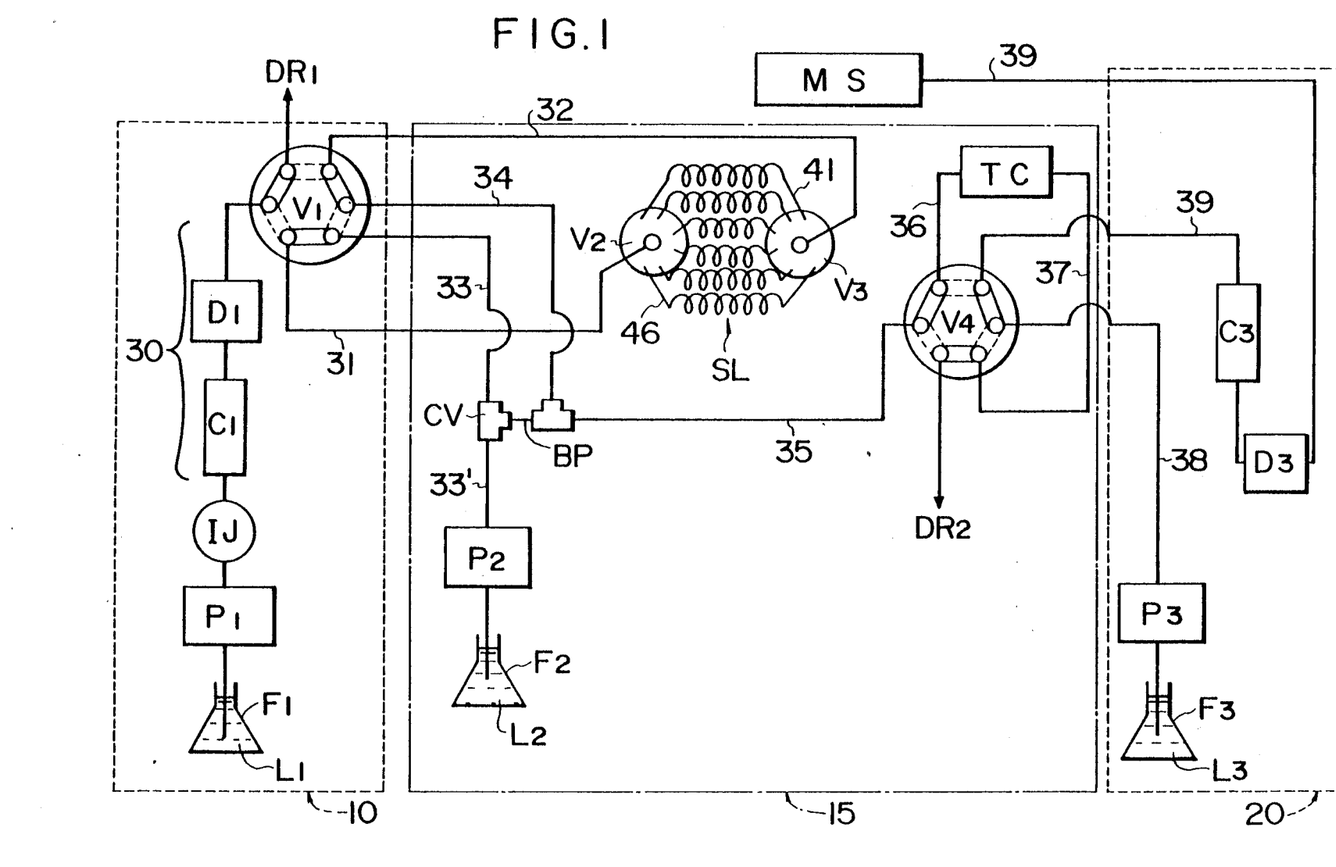
FIG. 1 is the schematic explanatory drawing of the high-performance liquid chromatography mass spectrometric apparatus which is an example of this invention.

In FIG. 1, (10) is 1st section where separation is carried out. ($F_1$) is a container in which the mobile phase A ($L_1$) for separating the aimed components is present, and the mobile phase A ($L_1$) is used for separating the aimed components by selecting appropriately the optimum buffer.

($P_1$) is a pump, (IJ) is an injector, ($C_1$) is a separating column, ($D_1$) is a detector, ($V_1$) is a six-port valve for changing over the line, ($DR_1$) is a discharging drain for discharging the unnecessary components together with the mobile phase A, and these are connected to each other by means of the lines comprised of stainless pipes and the like.

Figure 2:
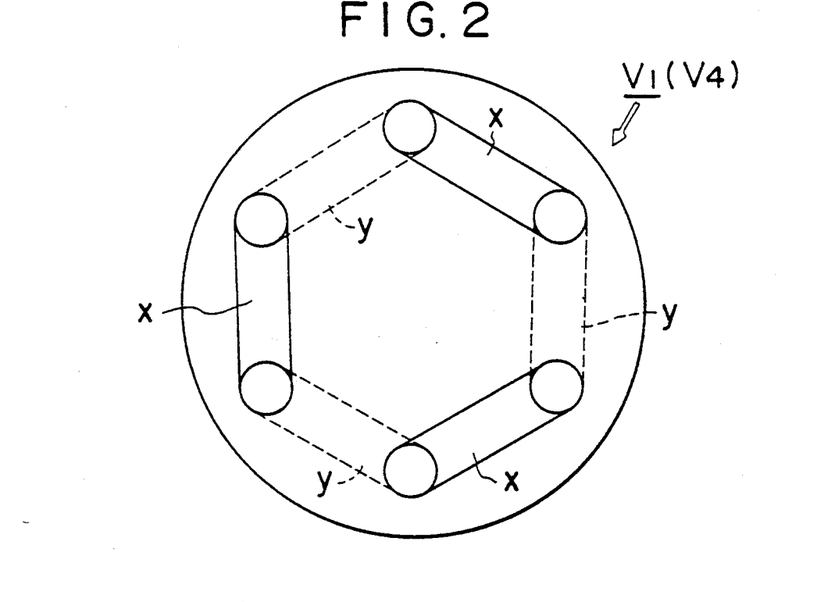
FIG. 2 is the schematic explanatory drawing of six-port valves ($V_1$) and ($V_4$).

FIG. 2 indicates the changing state of lines performed by six-port valve ($V_1$), and said changing state is set up in such a way that the lines connecting to six-port valve ($V_1$) may be changed over to full lines (x) or dotted lines (y) by operating alternately a cock (not shown).

In FIG. 1, (20) is 3rd section which sends the components separated in 1st section into a mass spectrometer (MS), and ($F_3$) is a container holding the mobile phase B ($L_3$) in it. For the mobile phase B ($L_3$), it is used a mobile phase containing a volatile buffer and a matrix necessary to elute the components from a trapping column (TC) described below, for example, the mixed solution of methanol or acetonitrile and acetic acid buffer or the like can be used; however the mobile phase suitable for a substance is appropriately used. In addition, ($P_3$) is a pump, ($C_3$) is a separating column, and ($D_3$) is a detector.

There is 2nd section (15) between 1st section (10) and 3rd section (20), ($F_2$) is a container full of a dilute solution ($L_2$) for diluting the mobile phase, ($P_2$) is a pump, (BP) is a diluting by-pass through which the dilute solution passes, (SL) is a sampling part, ($V_2$) and ($V_3$) are changing valves for changing over the loop of the sampling part (SL).

In addition, the constitution is set up in such a way that the flow rate of the dilute solution ($L_2$) which is poured from a by-pass may be adjusted by a flow rate-adjusting valve (CV).

Figure 3:
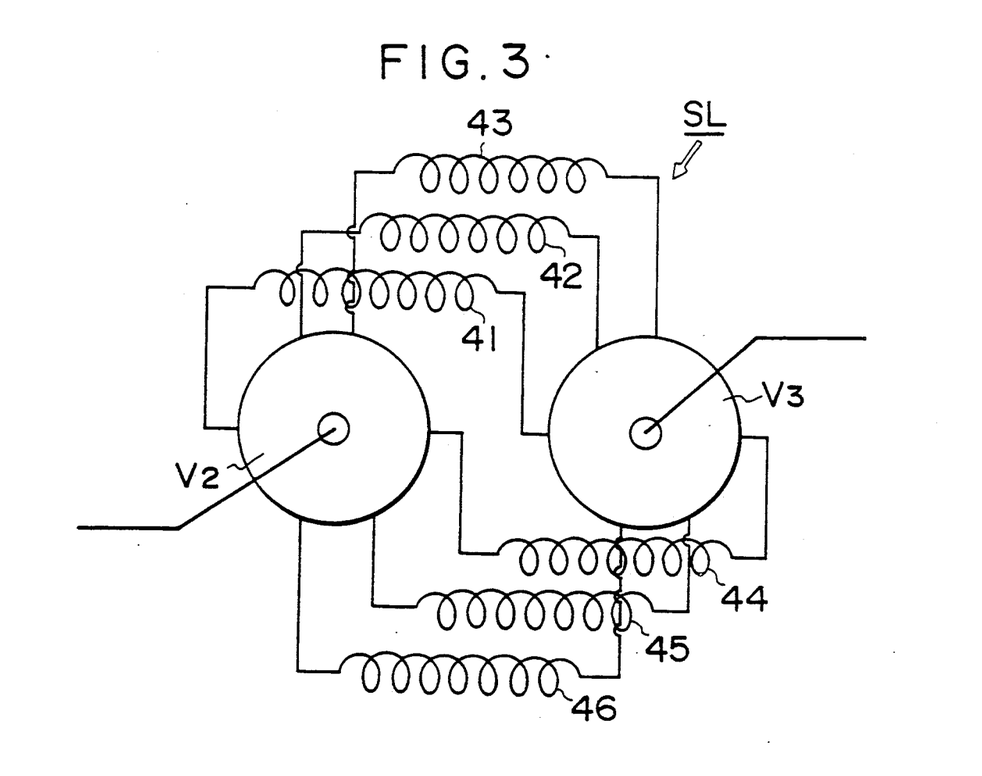
FIG. 3 is the schematic explanatory drawing of a sampling part.

As shown in FIG. 3, the sampling part ($S_1$) is equipped with 6 loops from loop (41) to loop (46) in order that the pathway through which the mobile phase passes can be selectively changed over to an optional loop by changing the change-over valves ($V_2$), ($V_3$). In addition, the number of the loops can be optionally decided, for example, the number of the loops can be more increased by installing more change-over valves.

Thus, the components are separated in 1st section (10) in order that the separated components may be divided into different component groups (41)-(46) respectively and retained separately.

($V_4$) is a six-port valve for changing the lines, ($DR_2$) is a discharging drain, and (TC) is a trapping column. The six-port valve ($V_4$) can change over the path as illustrated beforehand in FIG. 2. For the trapping column (TC), a column of the same mode as column ($C_3$) is used so as to adsorb the aimed components; however, a column specially designed for the high-performance liquid chromatography is not necessarily used, and any column having a certain degree of pressure resistance can be used. In accordance with the substance to be separated and analyzed, the columns ($C_1$) and ($C_3$) are also appropriately selected from the various modes of columns, for example, in view of a normal phase, reversed phase, ion exchange, gel permination chromatography (GPC), hydrophobic chromatography, affinity, optical resolution chromatography, and the like.

The exchange means of the mobile phase shall be illustrated below using the apparatus of this invention constituted above.

Further, lines connected to each part are (30) to (39) as shown in FIG. 1. First of all, in 1st section (1st process), a mobile phase A ($L_1$) is sent into a line (30) by operating a pump ($P_1$), and a sample is injected from an injector (IJ). The sample passes through the separating column ($C_1$) together with the mobile phase A ($L_1$), and there the sample is separated into each component contained in the sample, then each separated component is monitored by the detector ($D_1$).

Next, in 2nd section (2nd process), each component present in the mobile phase A is sent through the six-port valve ($V_1$) into the line (31) and there is retained in the prescribed loops (41) to (46) respectively.

In addition, changing-over of the valves ($V_2$) and ($V_3$) is performed in accordance with the detecting signal of the detector ($D_1$) in order that each component contained in the sample may be retained in each different loop.

As mentioned above, a proper quantity of the components is gathered in the loop; thereafter, the operation of the pump ($P_1$) is stopped, and the line (33) and the line (31) are communicated with each other by changing over the six-port valve ($V_1$).

In this state, by operating a pump ($P_2$) the dilute solution ($L_2$) for the mobile phase present in a container ($F_2$) is sent into the sampling part (SL) from lines (33'), (33), valve ($V_1$) and line (31), the components are pushed out together with mobile phase A ($L_1$) and passed through line (32), valve ($V_1$) and lines (34), (35), then introduced into a trapping column, and the components are caught by the trapping column (TC).

Also, in this case, while pouring a proper quantity of the dilute solution ($L_2$) for dilution of the mobile phase from the by-pass (BP), the components sent into the trapping column (TC) while adjusting the dilution ratio of the mobile phase, which facilitates to catch the components by the trapping column (TC). That is to say, the dilution ratio of the mobile phase easily caught by the trapping column (TC) are different respectively according to the kinds of the components so that the dilution ratio must be changeable so as to catch the component by the trapping column (TC) easily. When a proper quantity of the dilute solution ($L_2$) used for dilution of the mobile phase A is poured therein from the by-pass used for dilution of the mobile phase A in order to adjust the dilution ratio of the mobile phase A suitable for the components, the trapping column (TC) facilitates to catch the components.

In addition, the constitution is set up in such a way that the dilute solution ($L_2$) sent from a line (33') by operating the pump ($P_2$) is divided into two portions, one portion is poured into the intermediate part situated between line (34) and line (35) from the by-pass (BP), and another portion is made to pass through line (33) and to push out the components present in the sampling part (SL) together with the mobile phase A ($L_1$). Therefore, for instance, if the degree of valve opening can be changed by providing a flow rate-adjusting valve (CV) in the by-pass (BP), the pouring amount of the dilute solution used for diluting the mobile phase A can be easily adjusted according to the kinds of the components so that the best dilution ratio to a component can be obtained so as to catch the component by trapping column (TC) easily.

The object of the dilute solution ($L_2$) is also to catch the aimed components by the trapping column (TC) and to further remove the buffer present in the mobile phase A ($L_1$) used 1st section (10), for example, in the reversed phase system water and the like can be used and in the normal phase system hydrocarbon and halogenated hydrocarbon (e.g., hexane, chloroform, and the like) can be used. Thus, the components and the mobile phase A are diluted and made to pass through a line (35) and sent through a line (36) into the trapping column (TC), where the components are caught. And, the mixed solution of the mobile phase A ($L_1$) and the dilute solution ($L_2$) passes through the trapping column (TC), goes via a line (37) and the six-port valve ($V_4$), and is discharged from a discharged from a discharging drain ($DR_2$).

Next, in 3rd section (3rd process), the components collected in the trapping column (TC) are made to pass through a line (37) by changing over the six-port valve ($V_4$). In this state, by operating the pump ($P_3$) a mobile phase B ($L_3$) is sent to the line (38); then by sending the mobile phase B into the trapping column (TC) from the opposite direction (from a line (37) via the valve ($V_4$)) the mobile phase B ($L_3$) is sent through trapping column and the line (36), valve ($V_4$), line (39) and into the mass spectrometer (MS) and is analyzed.

Accordingly, the mobile phase A ($L_1$) used in 1st section (10) is rejected by the above-mentioned means and in 3rd section (20) the components are introduced into the mass spectrometer (MS) by using the mobile phase B ($L_3$), in order that the optimum mobile phase A ($L_1$) suitable for separating the components may be selected, and also the buffer and the matrix may be freely selected and added.

Thus, as shown in FIG. 1, if the constitution is set up in such a way that in 3rd section (20) the separating column ($C_3$) is further installed, the components are again separated into each component by this column ($C_3$), each component is detected by the detector ($D_3$) and is mass analyzed by the mass spectrometer (MS). Therefore, more precise mass spectrometry can be achieved and the reliability of analysis is enhanced by performing further separation by means of the separating column ($C_3$), even if the aimed components could not be separated satisfactorily in 1st section (10).

Also, as the results of the experiments, it was found that in case of installing the separating column ($C_3$) in 3rd section (20), if line (36) was composed of a thick pipe whose inside diameter was larger than that of other lines, separation by the separating column ($C_3$) could be better performed.

In addition, computerized control is possible for operating each pump or for changing-over the valve, the number of containers ($F_1$), ($F_2$) and pumps ($P_1$), ($P_3$) can be more increased, and the general-purpose properties of this apparatus can be more enhanced by selecting appropriately the suitable one from many kinds of mobile phases. Also, in accordance with the object, it is preferable to use a large-sized column for the separating column ($C_1$), and when the mass spectrometer is frit FAB method it is preferable to use a semimicro bore column (inside diameter is about 20–30 mm, length is about 10–30 cm; on the other hand, as for ordinary column, inside diameter is about 4.0–6.0 mm, length is about 10–30 cm) or a micro bore column (inside diameter is about 0.3–1.2 mm, length is about 10–30 cm) for the separating column ($C_2$).

And, separating effect can be more exhibited by changing the separating mode of 1st section (10) and 3rd section (20).

EXPERIMENT

The results of experiment which was performed by using the apparatus of the present invention shall be illustrated.

Experiment 1

A sample containing each 10 μg of tocopherol homologue α, β, γ and δ respectively was used in this experiment. In 1st section (10), the experiment was performed under the condition that the separating column ($C_1$) was Inertsil ODS-2 (4.6φ×150 mm made by Gaschro Kogyo Co., Ltd.), mobile phase A ($L_1$) was methanol, detection was at UV 275 nm, flow rate was 1.0 ml/min.

In the 3rd section (20), the experiment was performed under the condition that the column ($C_3$) was Inertsil ODS-2 (0.7$\phi$×150 mm made by Gaschro Kogyo Co., Ltd.), mobile phase B ($L_3$) was methanol containing 0.5% glycerol, detection was at UV 275 nm, flow rate was 0.02 ml/min.

And, dilute solution ($L_2$) was a mixed solution (10:90) of methanol and water, the flow rate was 0.5 ml/min. The trapping column (TC) was Inertsil ODS-2 (2.1$\phi$×50 mm, made by Gaschro Kogyo Co., Ltd.), the mass spectrometer was Frit FAB System Mass Spectrometer (JOEL JMS-HX 100, made by Nippon Denshi Co., Ltd.).

Figure 4:
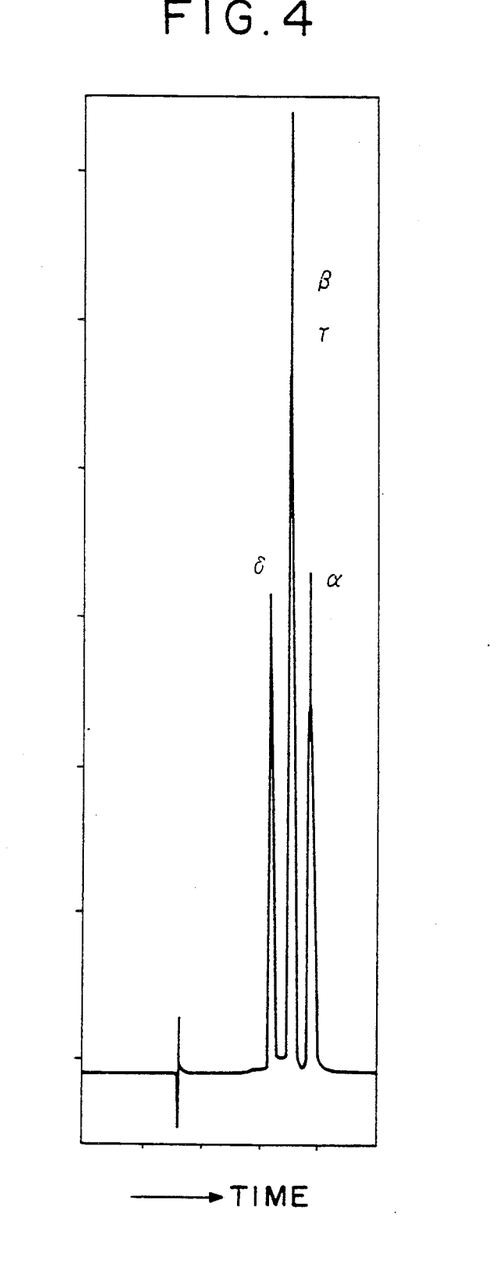
FIGS. 4, 5 are chromatograms of α-tocopherol by a detector ($D_1$) and a detector ($D_2$) respectively.
Figure 5:
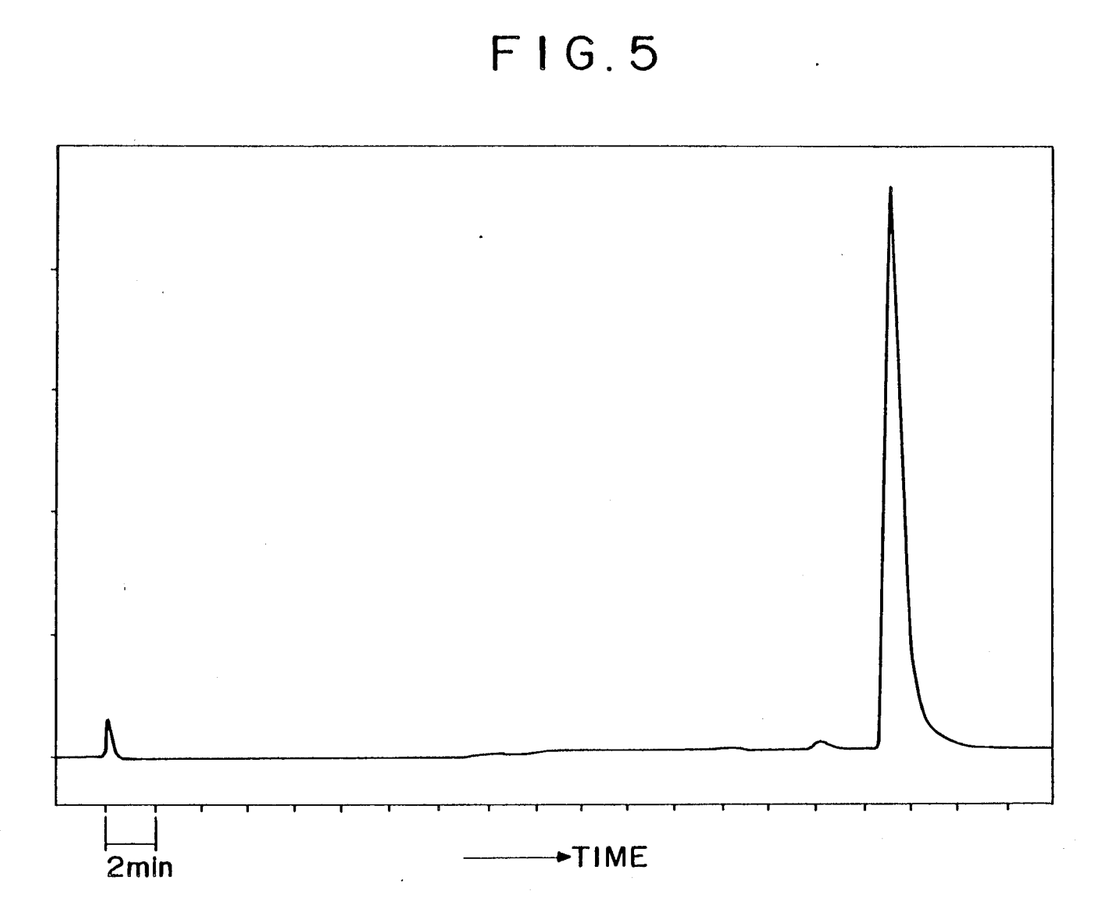
Figure 6:
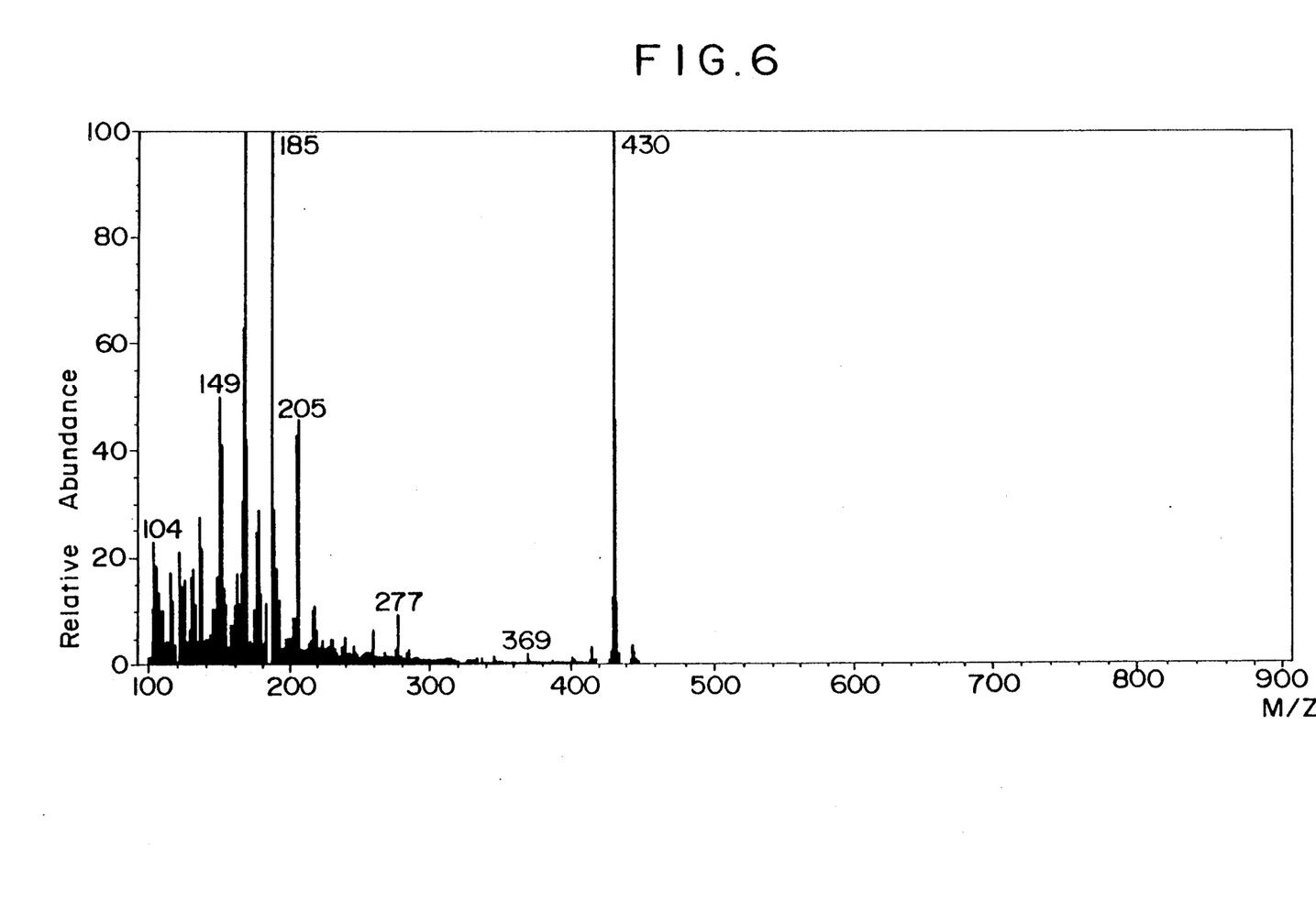
FIGS. 6, 7 are the mass spectrograms of -tocopherol analyzed by the mass spectrometer.

In 1st section (10), the detector ($D_1$) monitored that $\alpha$-tocopherol was separated and eluted (see FIG. 4), and the separated $\alpha$-tocopherol was taken in the sampling part (SL) by changing over a valve ($V_1$). In addition, the dilute solution ($L_2$) was sent, $\alpha$-tocopherol was caught by the trapping column (TC) and was monitored by the detector ($D_3$) (see FIG. 5). Then $\alpha$-tocopherol was introduced into the mass spectrometer (MS) and analyzed. The mass spectrogram obtained in this analysis was shown in FIG. 6. As seen from FIG. 6, the molecular ion peak 430 of $\alpha$-tocopherol could be measured with high sensibility.

Figure 7:
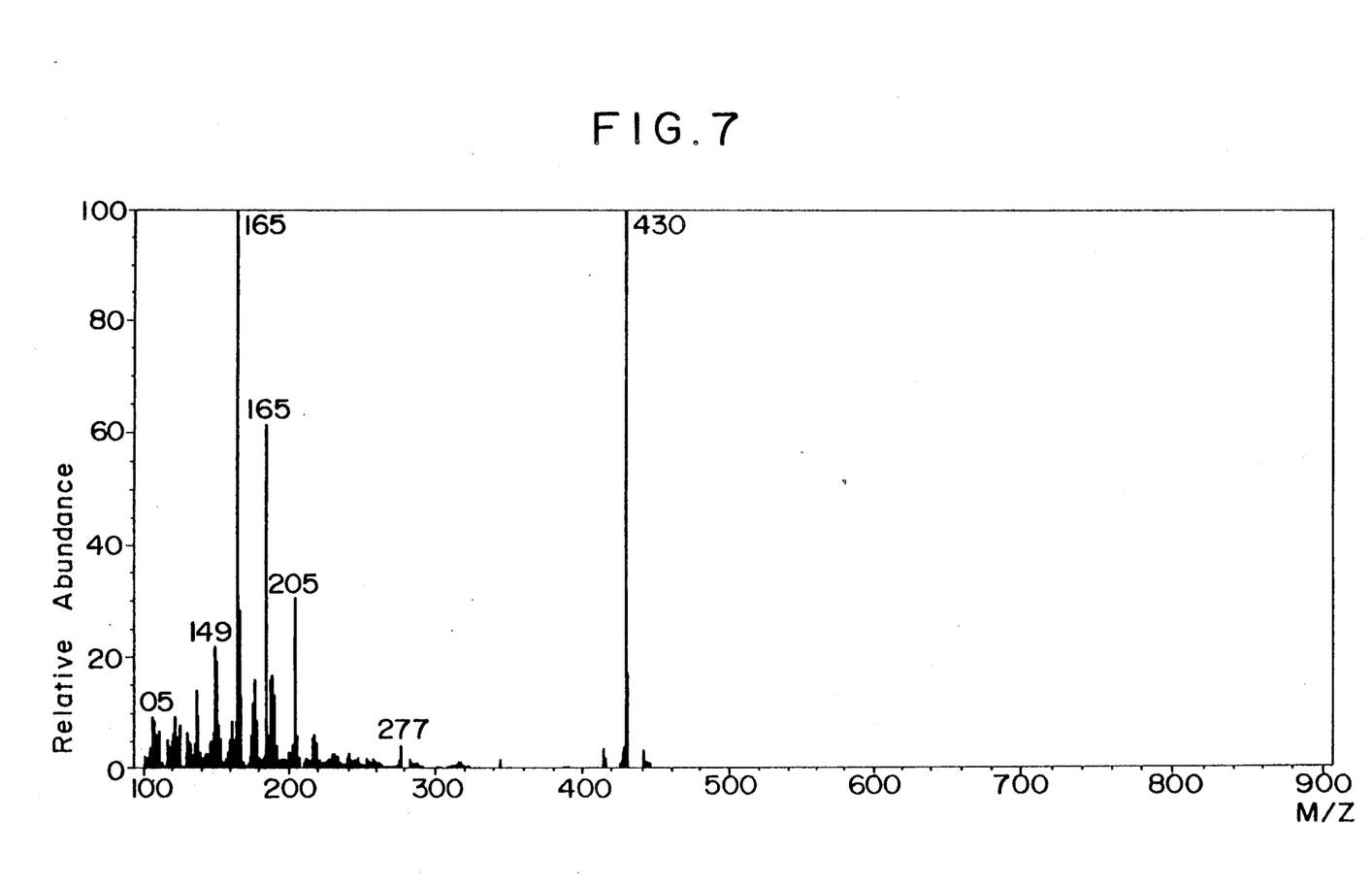

On the other hand, in 1st section (10) a 1.25% phosphoric acid was added into the mobile phase A and the mass analysis was performed, as a result the molecular ion peak 430 of $\alpha$-tocopherol could be measured with high sensibility without showing any influence caused by the addition of phosphoric acid which is a non-volatile buffer (see FIG. 7).

As mentioned above, the mass analysis was performed by using this apparatus without showing any influence even if non-volatile buffer such as phosphoric acid which restricts ionization necessary for the mass analysis was used.

Experiment 2

The degree of separating effect in 3rd section (20) was examined after $\alpha$-tocopherol 1 g being caught by the trapping column (TC) in cases of the separating column ($C_3$) being installed in 3rd section (20) and not installed.

The experiment was carried out under the condition that in 3rd section (20), a column ($C_3$) was Inertsil ODS-2 (0.7×150 mm made by Gaschro Kogyo Co., Ltd.) a mobile phase B ($L_3$) was a solution (80:20) of methanol, detection was carried out at UV 282 nm, flow rate was 0.02 ml/min, dilute solution ($L_2$) used for diluting the mobile phase was a mixed solution (30:70) of methanol and water, flow rate was 1.0 ml/min, trapping column (TC) was Inertsil ODS-2 (4.0$\phi$×10 mm made by Gaschro Kogyo Co., Ltd.). As a result, if the constitution is set up in such a way that in 3rd section (20) the separating column ($C_3$) is further installed after the components caught by the trapping column (TC), each component was concentrated and separated satisfactorily.

Figure 8:
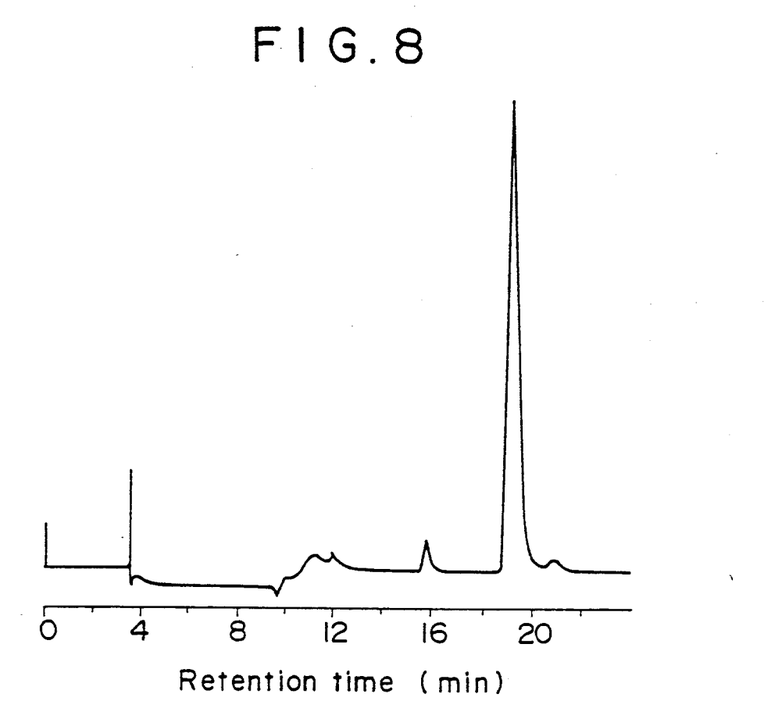
FIG. 8 is a chromatogram of Experiment 2 wherein a column ($C_3$) for separating the components is used.

That is to say, in case of installing the separating column ($C_3$) in 3rd section like this invention, the state monitored by the detector ($D_3$) was obtained as shown in FIG. 8, after having the components passed, the result indicating a remarkable sharp peak was obtained.

Figure 9:
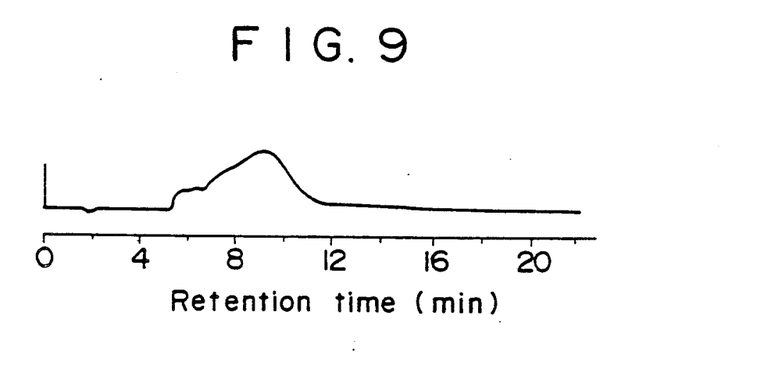
FIG. 9 is a chromatogram wherein the column ($C_3$) is not used in case of FIG. 8.

On the contrary, in case of non-installing the column ($C_3$) wherein each component was introduced into the detector ($D_3$) from the trapping column (TC) directly, the state monitored by the detector ($D_3$) was obtained as shown in FIG. 9, the result indicating a broad peak was obtained. As mentioned above, by installing the column ($C_3$), each components was concentrated and introduced into a mass spectrometer (MS), so that it was found that the concentrating effect of the column ($C_3$) can be more exhibited.

Experiment 3

Each 1 $\mu$g of $\alpha$, $\beta$, and $\delta$-tocopherol was respectively caught at the same time by the trapping column (TC) and separated by the separating column ($C_3$) placed in 3rd section.

The experiment was carried out under the condition that in 3rd section (20), a column ($C_3$) was Inertsil ODS-2 (0.7×150 mm made by Gaschro Kogyo Co., Ltd.) a mobile phase B was methanol, detection was carried out at UV 275 nm, flow rate was 0.02 ml/min, dilute solution ($L_2$) used for diluting the mobile phase A was a mixed solution (30:70) of methanol and water, flow rate was 1.0 ml/min, trapping column (TC) was Inertsil ODS-2 (4.0$\phi$×10 mm made by Gaschro Kogyo Co., Ltd.).

Also, the apparatus was constituted in such a way that only the inside diameter of lines (30)–(39) was 0.1$\phi$, then experiment was carried out.

$\alpha$, $\beta$ and $\delta$-tocopherol eluted in 1st section were intentionally mixed and taken in the same loop of the sampling part (SL) without changing over the valve ($V_1$). Thus, $\alpha$, $\beta$, and $\delta$-tocopherol were caught by the trapping column (TC) in the mixed state, and the separation was performed by means of the separating column ($C_3$) placed in 3rd section (20) by changing over the valve ($V_4$).

Figure 10:
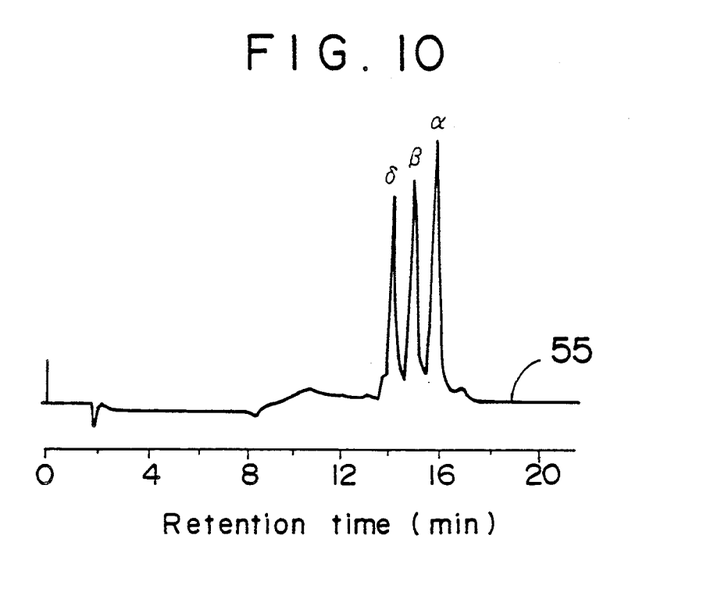
FIG. 10 is a chromatogram of Experiment 3 wherein the sample is α, β, and δ-tocopherol.

As mentioned above, the state wherein $\alpha$, $\beta$ and $\delta$-tocopherol were being separated was monitored by a detector ($D_3$), as a result, it was found that said state was shown as the zigzag line (55) of FIG. 10, and the mixed tocopherols could be separated into $\alpha$, $\beta$ and $\delta$-tocopherol respectively.

As a result, it was found that even if the aimed components could not be satisfactorily separated in 1st section (10), highly precise mass spectrometry with sharpness of separation could be performed, and the reliability of analysis could be enhanced by setting up the constitution wherein further separation was carried out by the separation column ($C_3$) installed in 3rd section (20).

Experiment 4

The experiment was performed under the condition that the diameter of the separating column ($C_3$) in 3rd section which was smaller than Experiment 2 was 0.4$\phi$×150 mm. It was recognized the relation between the diameter of pipe in line (36) and the separation.

Each 1 $\mu$g of $\alpha$, $\beta$, and $\delta$-tocopherol was restectively caught at the same time by the trapping column (TC) and separated by the separating column ($C_3$) placed in 3rd section (20). Further the experiment was carried out under the condition that in 3rd section (20), a column ($C_3$) was Inerstil ODS-2 (0.4$\phi$×150 mm made by Gaschro Kogyo Co., Ltd.) a mobile phase B ($L_3$) was a mixed solution (80:20) of methanol and ethanol, detection was carried out at UV 282 nm, flow rate was 0.01 ml/min, dilute solution ($L_2$) used for diluting the mobile phase was a mixed solution (30:70) of methanol and water, flow rate was 1.0 ml/min, trapping column (TC) was Inertsil ODS-2 (0.4$\phi$×10 mm made by Gaschro Kogyo Co., Ltd).

Figure 11:
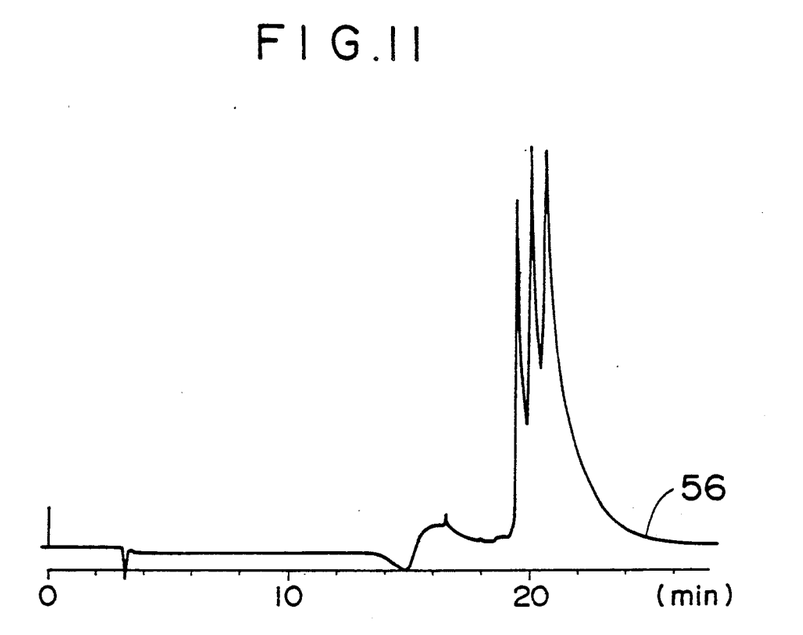
FIG. 11 is a chromatogram wherein the whole lines are constituted with stainless pipes whose inside diameter is 0.1 mm.
Figure 12:
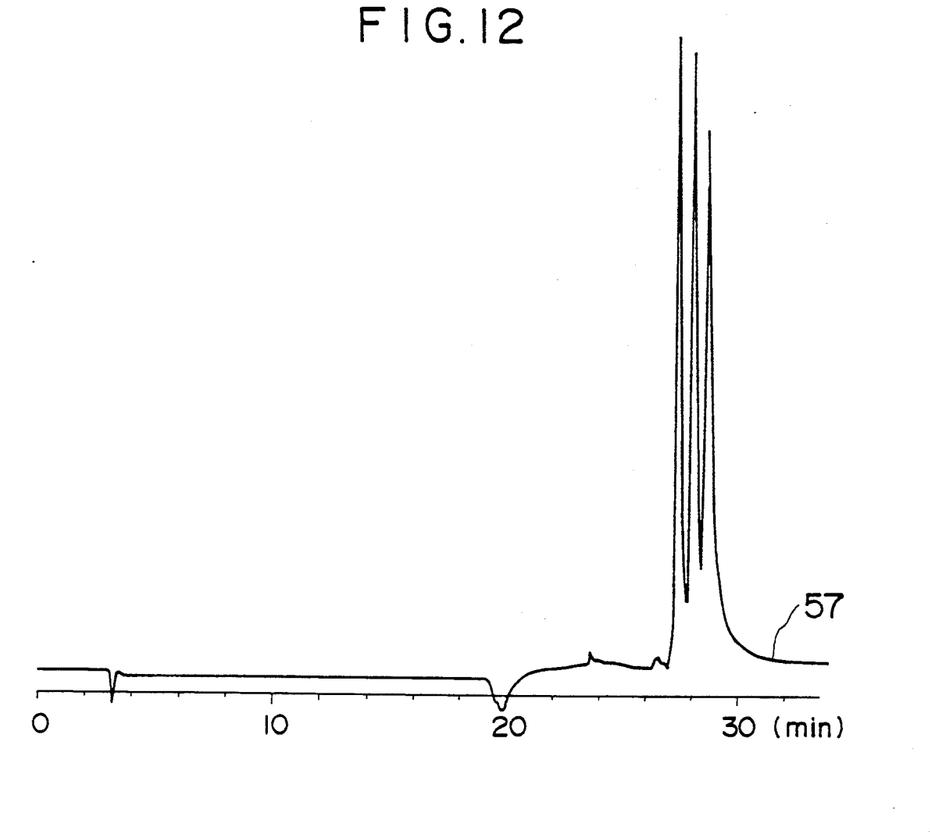
FIG. 12 is a chromatogram wherein only a line (36) is constituted with wide stainless pipe whose inside diameter is 0.8 mm.

When all the lines were constituted with pipes whose inside diameter was 0.1 mm, the state wherein the components were being separated was monitored by the detector ($D_3$). As a result, the curved line (56) of FIG. 11 was obtained, and the better separation could not be performed. However, the state wherein a pipe whose inside diameter was 0.8 × 100 mm was used only for the line (36) and other lines were constituted with stainless pipes whose inside diameter was 0.1 mm was monitored, then the curved line (57) was obtained as shown in FIG. 12 so that the separation between the components could be better performed.

As a result, it was found that if line (36) was constituted with a thick pipe whose inside diameter was larger than that of other lines, separation by the separating column ($C_3$) could be better performed.

In addition, it is considered that when the inside diameter of the separating column ($C_3$) is decreased and that of the line (36) is increased, the gradient effect for separation has been generated in the line (36).

Experiment 5

In the present invention, the optimum mobile phase A and B suitable for separating the components may be selected respectively for the separating column ($C_1$) and ($C_3$). Also separating effect can be more exhibited by selecting the separating mode of the column ($C_1$) and ($C_3$).

The analysis for a plasma sample containing verpamil was performed by using a reversed phase mode of the column ($C_1$) and optical resolution mode of the column ($C_3$) respectively so that verpamil was separated in the column ($C_1$) and further an optical isomer was separated in the column ($C_3$).

In first section (10) a column was Inertsil ODS-2 (4.6$\phi$ × 150 mm made by Gaschro Kogyo Co., Ltd.), mobile phase A was a mixed solution (3:7 pH=3.0) or acetonitrile containing 5 mM 1-pentane sodium sulfonate:water, detection was carried out at UV 230 nm, flow rate was 1.0 ml/min; in 3rd section (20), a column was Ultron ES-OVM (4.6 1D × 150 mm made by Shinwa Kako Co., Ltd.), mobile phase B was a mixed solution of tetrahydrofuran:ethanol:water (1:8:91), detection was carried out at UV 230 nm, flow rate was 1.0 ml/min.

And, the dilute solution ($L_2$) used for diluting the mobile phase was a mixed solution (pH=7.5) of 5 mM dipotassium hydrogen phosphate and potassium dihydrogen phosphate, flow rate was 4.0 ml/min, a trapping column (TC) was Ultron ES-OVMG (10 mm × 4.0 mm 1D made by Shinwa Kako Co., Ltd).

In the same manner as Experiment 1, the state where verapamil was separates and eluted in 1st section (10) was monitored by the detector ($D_1$), and the verapamil was taken in the sampling part (SL) by changing over the valve ($V_1$). The chromatogram (50) of FIG. 13 shows the monitored state by detector ($D_1$), and a peak (51) indicates that verapamil has been detected.

After thus sampling verapamil, verapamil was caught by means of the trapping column (TC) by sending the dilute solution ($L_2$), therefore, verapamil was again separated by the separating column ($C_3$) placed in 3rd section (20) by changing over the valve ($V_4$).

Figure 13:
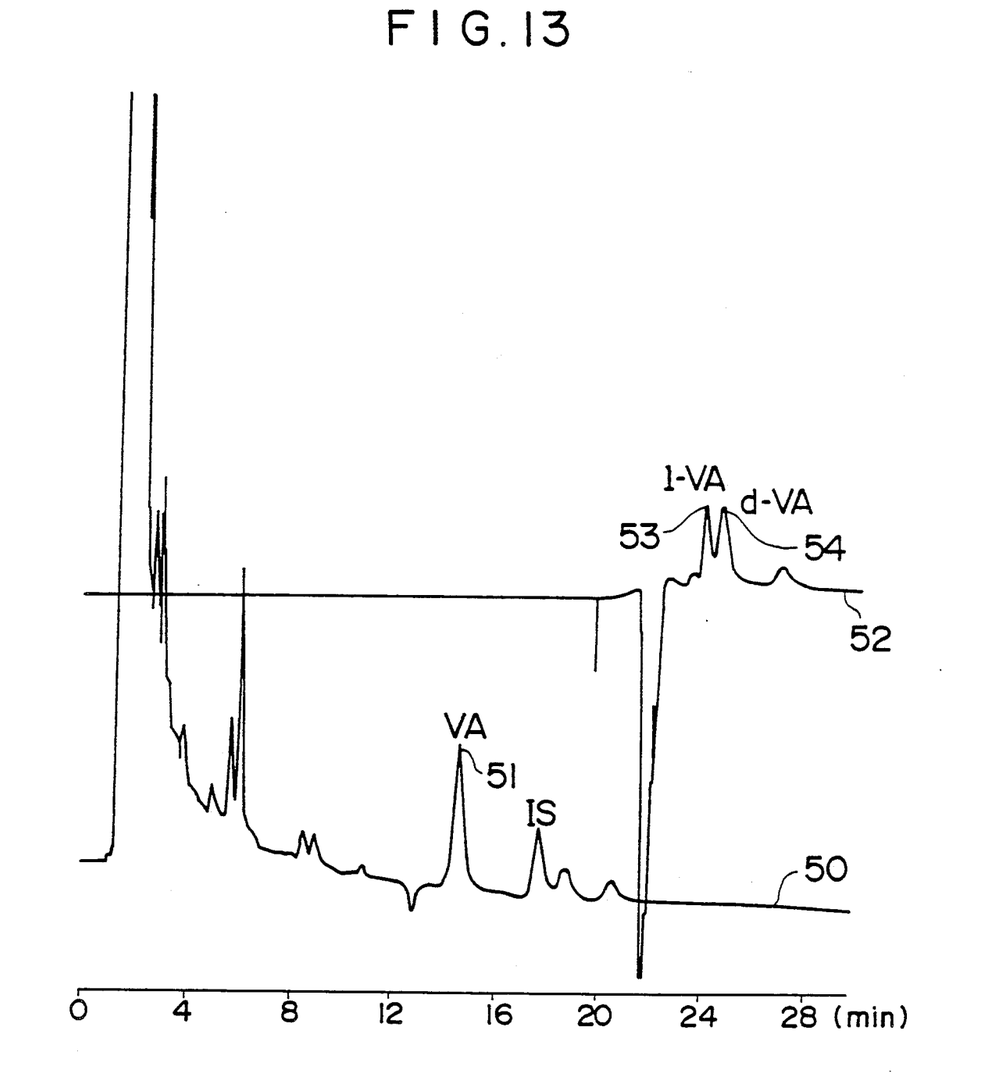
FIG. 13 is a chromatogram of Experiment 5 wherein the sample is verapamil.

As mentioned above, the state wherein verapamil was again separated by the separating column ($C_3$) was monitored by the detector ($D_3$), and then said state was indicated as the chromatogram (52) of FIG. 13. As the result of analysis of this curved line, it was found that at a peak (53) the D (dextro-rotatory) substance of verapamil had been separated, and at a peak (54) the L (levo-rotatory) substance of verapamil had been separated.

As for Experiment 2 through 5 it was found that the installation of the separating column ($C_3$) in addition to that of the separating column ($C_1$) is very useful in the system of the present invention.

While the invention has been particularly shown and described with reference to the preferred embodiment thereof, it will be understood by those skilled in the art art that the foregoing and other changes in form and details can be made therein without departing from the spirit and scope of the invention.

What is claimed is:

1. In a method of high performance liquid chromatography mass spectrometry, where a sample having an analytical object therein injected into a liquid mobile phase A, components of the analytical object are separated in mobile phase A in a separation column, mobile phase A is separated from the components and the components analyzed in a mass spectrometer, the improvement comprising:

(1) diluting mobile phase A having the separated components therein with a diluent to form a diluent solution thereof;

(2) passing a dilute solution to a trapping column, trapping the separated components therein and discharging the diluent and mobile phase A therefrom;

(3) eluting the trapped components from the trapping column by passing a mobile phase B therethrough and forming a solution of components in mobile phase B, and wherein mobile phase B is different from mobile phase A; and (4) passing the solution to a mass spectrometer where mobile phase B is separated from the components and the components were analyzed.

2. The method of claim 1, wherein the components trapped by the trapping column and eluted into mobile phase B are further separated in mobile phase B in a second separation column.

3. The method of claim 1, wherein components separated in the mobile phase A and before said dilution step are retained in separate retainers of a sampling part such as to collect increased amounts of each component in mobile phase A for subsequent analysis.

4. The method of claim 3, wherein said dilution step is carried out such as to displace the separated components and mobile phase A from each retainer and pass the same to said trapping column.

5. The method of claim 1, wherein mobile phase A is non-volatile.

6. In an apparatus for high speed liquid chromatography mass spectrometry, wherein means are provided for injecting a sample having an analytical object therein into a mobile phase A, a separation column separates in the mobile phase A components of the analytical object, and a mass spectrometer separates the components from mobile phase A and analyzes the components, the improvement comprising:

(1) means for diluting mobile phase A having the separated components therein with a diluent to form a diluted solution thereof;

(2) a trapping column for trapping the separated components therein and discharging the diluent and mobile phase A therefrom;

(3) means for passing a mobile phase B through said trapping column so as to elute the trapped components from the trapping column and form a solution in mobile phase B, and wherein mobile phase B is different from mobile phase A; and (4) means for passing the solution to a mass spectrometer for separation of mobile phase B and analysis of the components.

7. The apparatus of claim 6, wherein a further separating column is disposed between the trapping column and the mass spectrometer.

8. The apparatus of claim 6, wherein retaining means for retaining separated components is disposed between said separating column and said trapping column.

9. The apparatus of claim 8, wherein a plurality of said retaining means are so disposed.

* * * * *